United States Patent [19]

Douglas

[11] Patent Number: 5,060,506
[45] Date of Patent: Oct. 29, 1991

[54] METHOD AND APPARATUS FOR MONITORING THE CONTENT OF BINARY GAS MIXTURES

[76] Inventor: David W. Douglas, 9323 Alden, Lenexa, Kans. 66215

[21] Appl. No.: 424,931

[22] Filed: Oct. 23, 1989

[51] Int. Cl.$^5$ ............................................. G01N 7/00
[52] U.S. Cl. .................................. 73/24.01; 73/19.03; 73/61 R; 73/597; 73/571
[58] Field of Search ................ 73/19.03, 24.01, 61 R, 73/597, 571

[56] References Cited

U.S. PATENT DOCUMENTS

4,630,482 12/1986 Traina .................................... 73/597
4,938,066 7/1990 Dorr ....................................... 73/597

Primary Examiner—Robert R. Raevis
Assistant Examiner—William Francos
Attorney, Agent, or Firm—Kokjer, Kircher, Bowman & Johnson

[57] ABSTRACT

A method and apparatus for continuously monitoring the ratio of gases in a two gas mixture such as a therapeutic oxygen/nitrogen mixture. The gas mixture is passed through a sample tube within which ultrasound waves travel in successive bursts of pulses at the resonant frequency of the transmitter/receiver pair. Between bursts is a quiescent time period having a duration long enough to assure dissipation of transients so that standing waves do not form. The delay caused by the transit time of the sound through the gas sample generates electrical pulses that are translated into an analog signal which is then temperature-corrected. The resulting voltage, which is proportional to the transit time and thus to the gas composition, is compared with adjustable reference voltages to trigger high and low audio/visual alarms. A digital display provides a constant readout of the percentage of the gas component having the highest molecular weight. The sample tube is contained inside a larger cylindrical body to enhance the gas flow and provide thermal insulation which allows temperature compensation to be accurately performed.

16 Claims, 4 Drawing Sheets

METHOD AND APPARATUS FOR MONITORING THE CONTENT OF BINARY GAS MIXTURES

BACKGROUND OF THE INVENTION

This invention relates generally to the analysis of gases and deals more particularly with a method and apparatus which makes use of ultrasound to monitor the ratio of gases in a binary mixture such as a therapeutic air/oxygen mixture.

In the analysis of gas mixtures containing several different gases, complicated and expensive techniques such as mass spectrometry are often employed. For example, air pollution studies typically require complex methods of analysis involving numerous procedures for identifying and quantifying the gases present in a sample. Even the analysis of simpler gas mixtures normally requires the use of measurement techniques which are specific for the gases involved and which require frequent calibration, replenishment of reagent chemicals, and other awkward, costly and time consuming procedures.

Frequently, the objective is to continuously monitor the ratio of only two gases of known identity. In such cases, the measurement system need not be specific for the gases involved since their identity is known, and it is normally important for the equipment and technique to be simple, reliable and inexpensive. By way of example, oxygen/nitrogen mixtures are used in the therapeutic administration of oxygen from oxygen concentrators in home healthcare. Additionally, respirators, ventilators and air/oxygen blenders are commonly used in hospitals. There are other medical applications aside from the obvious ones in anesthesia. All of these involve what can be treated as binary mixtures.

Other important applications for binary gas analysis exist outside the field of medicine. For example, high altitude aircraft produce oxygen by using oxygen concentrators. Also, large volume oxygen concentrators are being increasingly used for welding, particularly in third world countries where delivery of tanked oxygen is difficult. Applications also exist in underwater vehicles and in some mines.

Of the oxygen monitors that are commercially available, the only ones presently feasible for the purposes recited above utilizes either a fuel cell or a polarigraphic half-cell, which not only makes these devices unduly expensive but also requires frequent cell and electrolyte replacement because they are rapidly consumed in a high oxygen environment. Both types of units are overly sensitive to changes in temperature and in general are poorly temperature compensated. They are also sensitive to changes in barometric pressure. Moreover, these monitors respond sluggishly to changes in gas composition, requiring typically one minute to equilibrate to large changes. For these and other reasons, they are poorly suited for use by lay people and/or in unattended applications.

Although it has long been known that acoustical techniques can be used for gas analysis, severe technical problems have been encountered when attempts are made to analyze gases by using acoustic waves. These problems are acoustical, mechanical, electronic and thermal, and they all contribute to the main problems caused by standing waves and temperature changes. In the past, continuous wave systems have been considered appealing because they permit the use of resonant transmitter and receiver elements, affording a good signal-to-noise ratio, high sensitivity and simplicity of design. However, the continuous-wave approach invites new problems, particularly within a closed transducer chamber. In particular, the transmitter element must have a mechanical resonant frequency that matches the driving frequency while the receiver element must be mechanically tuned to the anti-resonant frequency in order to provide the necessary low driving impedance and high receiving impedance. In a continuous-wave system, the receiver accepts acoustic energy from the transmitter within a transducer chamber and generates a signal, with phase shift affected by mean molecular weight and temperature of the gas, to the receiver circuit. The acoustical waves also reflect from the surfaces within the transducer chamber, thus setting up standing waves that frustrate repeatable measurements. In addition, upon excitation by the transmitted energy, the receiver retransmits a signal at its anti-resonant frequency in a complex fashion back toward the transmitter, and the result is a beat-frequency that has an unpredictable effect on response to temperature. in addition to the other problems normally associated with standing waves.

Ceramic transducers, though simple, sensitive and inexpensive, have widely varying temperature coefficients. In addition to the normal sound-in-gas temperature factor that is mathematically predictable, there are unpredictable temperature induced shifts in transducer capacitance and mechanical resonant frequency. There are also other more subtle variables that contribute to standing waves. For all of these reasons, even though they are useful for approximate triggering of low oxygen alarms in oxygen concentrators, gas analyzers based on the continuous-wave technique have inadequate accuracy and repeatability for requirements that are more sophisticated, such as these served by the present invention.

Most prior inventors who have adopted the continuous wave technique have failed to even recognize the standing wave problem, and those who do recognize the problem have not been able to successfully solve it. For example, U.S. Pat. No. 2,963,899 to Martin proposes filling the transducer chamber with granular material that is permeable to gas to prevent standing waves. However, filling the chamber in this manner entraps gas in small pockets and markedly slows down the response of the system to change in gas composition. U.S. Pat. No. 3,848,457 to Behymer and Japanese Patent No. 52-36089 to Koki show units that tune the driving frequency in order to deliberately establish a standing wave and then note deviations in loops and nodes with changes in gas composition. Both U.K. Patent No. 798,323 to Lawley and U.S. Pat. No. 4,220,040 to Noguchi recognize and directly address the standing wave problem. However, only Noguchi proposes a workable solution by damping the receiver and transmitter by way of "negative emittance amplifiers." These are essentially emitter-coupled flip flops which are said to present a short circuit across both transducer elements and thus damp them.

Another ultrasound technique used in the past is exemplified by U.S. Pat. No. 3,557,605 to Lanneau and U.S. Pat. No. 3,798,528 to Molyneuz. In this type of unit, a single electrical pulse is periodically applied to a nonresonant damped transmitter crystal, the acoustic impulse is delivered to a damped receiving crystal, and the transit time is measured. A variation of this is referred to as the "singaround" and is disclosed by U.S. Pat. Nos. 3,468,157 to Burke, 2,568,227 to Eligroth, 4,300,167 to Lorgini and 2,263,750 to Mikelson. The "sing-around" technique involves using the received impulse to retrigger the transmitter pulse, so that the frequency generated by this electro-acoustic loop varies with gas composition and temperature. Impulse methods avoid standing wave problems and thereby greatly improve the predictability of temperature behavior; however, they require the use of nonresonant transducer elements. They also lack the high sensitivity of the continuous-wave method, and they suffer a reduced signal-to-noise ratio due to the fact that transient noise spikes, such as those encountered in an environment with mechanically vibrating parts, can trigger false signals.

The effects of temperature on the speed of sound waves are well known. However, most of the prior attempts at monitoring gases have treated this phenomenon lightly and have failed to appreciate its considerable significance and complexity. U.S Pat. Nos. 3,557,605 to Lanneau and 4,425,804 to Mount control the temperature of the gas and/or its environment to a constant value, but in a compact and uncomplicated instrument this is difficult to do efficiently because of the inherently poor conductivity of the gas. Furthermore, the temperature of the sample gas that is introduced may differ considerably from that of the body of the transducer, as may occur within an oxygen concentrator. Another technique that has been proposed is to transmit ultrasound simultaneously through a standard gas as well as through the sample gas, as typified by U.S. Pat. No. b 2,984,097 to Kniazuk, U.S. Pat. No. 3,353,400 to Schafft and German Patent No. 3,009,566. Comparing the transit times cancels the direct temperature influence but does not eliminate standing waves. This approach is accurate only when the temperatures of the two gases are equal and this is not always the case. For example, there can be a significant temperature differential encountered when ventilating an accident victim with a warmed air/oxygen mixture in a freezing environment.

SUMMARY OF THE INVENTION

The present invention provides a gas analyzer that meets the need for a practical and economical monitor for oxygen concentration in a nitrogen/oxygen mixture. In a preferred embodiment of the invention, the percentage of oxygen is continuously displayed digitally, and an audio/visual alarm is triggered if the oxygen concentrations falls below or rises above limits that can be adjusted as desired. Response to a change in oxygen level is virtually immediate. Routine replacement of parts and calibration are unnecessary, and temperature stability is provided. Moreover, changes in atmospheric pressure, ambient vibration and noise have no adverse effects on the unit.

The present invention utilizes the physical phenomenon that sound waves travel at different velocities through different gases, so the principles of the invention are applicable to virtually all binary mixtures, the preferred one being the air/oxygen mixtures that are encountered most commonly in medical applications. The invention also overcomes the major problems encountered in ultrasound technology for gas analysis.

The velocity of sound through a gas at constant temperature is given by $V=(e/d)^{\frac{1}{2}}$, where V is the velocity, e is the adiabatic elasticity and d is the density. Pressure alters e and d proportionately, so pressure does not affect the velocity. Taking the effect of temperature into account and assuming there are no standing waves present or other disruptive phenomena, the velocity is $V=(eRT/M)^{\frac{1}{2}}$, where R is the universal gas constant, T is the temperature ($^{\circ}$K) and M is the molecular weight of the gas. In a binary gas mixture, by monitoring the velocity and taking the temperature into account, the mean molecular weight of the gas can be determined and thus their relative concentrations are revealed.

These physical principles are made use of in constructing a gas monitor having improved characteristics. An inner cylinder which provides a sample chamber for the gas is concentric with a larger outer cylinder forming the transducer housing. The use of coaxial cylinders is beneficial because it creates gentle flow of the gas through the inner cylinder and also because it assures substantially equal pressure inside and outside of the sample chamber. This physical construction avoids error caused by the mechanical displacement that can result from violent blasts of gas against the transducer elements and large pressure differences across the sample chamber wall.

Equally important, the physical construction of the transducer provides more accuracy in the temperature measurement of the gas. The inner and outer cylinders both provide thermal insulation, and they are separated by a gas space. The temperature sensor is mounted inside of the inner cylinder on an acoustical lining which insulates the sensor from the inner cylinder wall. The only path along which heat can move freely is provided by three small lead wires, and even these are stabilized at the gas temperature because the ga flows directly past them.

The inner cylinder is provided with a resonant transmitter at one end and with a resonant receiver at the other end which is only about 1.5 inches away from the transmitter to minimize the length of the transducer. It is an important feature of the invention that the transmitter is excited with sequential bursts of pulses which each contain a selected number of pulses at the resonant frequency of the transmitter. The successive bursts are separated by a quiescent time period having a duration long enough to allow all reverberations and transients to dissipate so that standing waves cannot form.

DESCRIPTION OF THE DRAWINGS

In the accompanying drawings which form a part of the specification and are to be read in conjunction therewith and in which like reference numerals are used to indicate like parts in the various views.

DETAILED DESCRIPTION OF THE INVENTION

Figure 1:
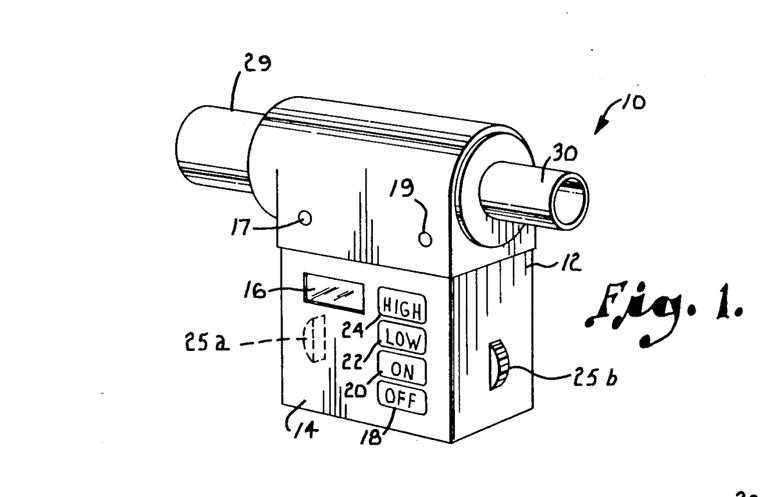
FIG. 1 is a perspective view of a binary gas monitoring device constructed according to the present invention.

Referring now to the drawings in more detail and initially to FIG. 1 in particular, numeral 10 generally designates a gas monitoring device constructed in accordance with the present invention and suitable for use in monitoring the relative concentration in a binary gas such as air (which is predominately nitrogen and oxygen). The gas monitoring device 10 has a body 12 which houses an acoustical transducer and electronic circuitry which will be described in more detail. The transducer is housed within the upper portion of the body 12, while the electronics are housed within the lower portion of the body. The lower portion of the body includes a front face 14 having a liquid crystal display (LCD) 16, an LED alarm indicator 17, an off switch 18, an audio alarm 19, an on switch 20, a low oxygen level adjustment switch 22 and a high level adjustment switch 24. The switches 18-24 are membrane type switches. From each side of body 12 protrudes the edge of a thumbwheel adjustment control. Left hand control 25a sets the low alarm limit while switch 22 is depressed to reveal the value of the alarm setting, and right hand switch 25b sets the high alarm limit while switch 24 is depressed for the same purpose.

Figure 2:
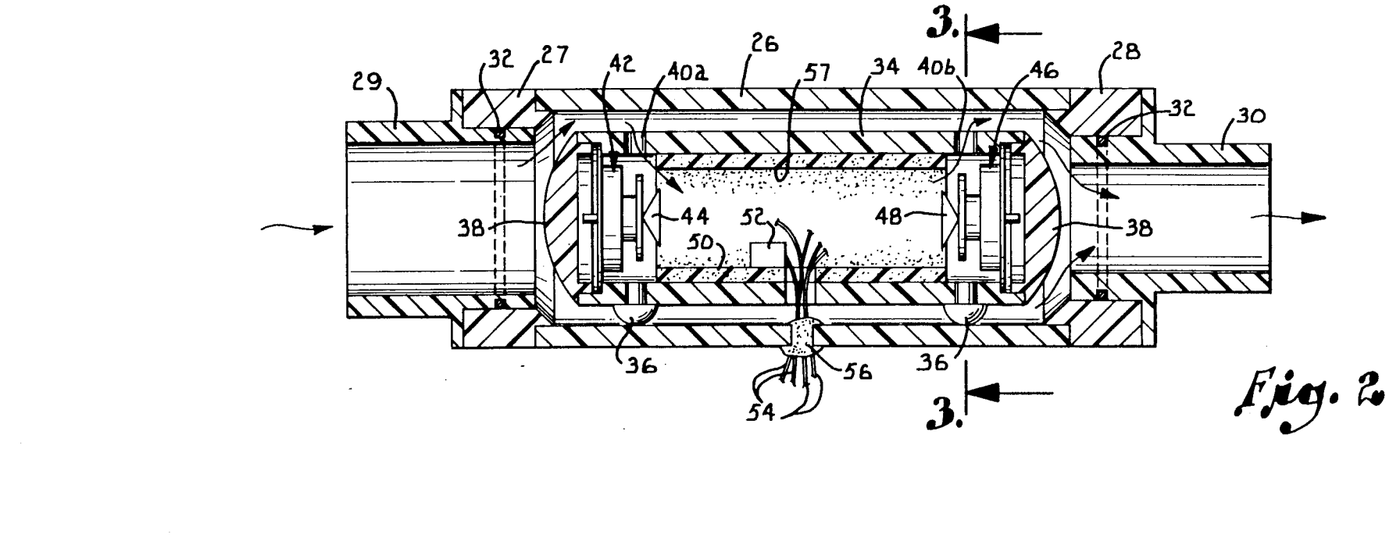
FIG. 2 is a cross sectional view taken through the transducer of the gas monitoring device.
Figure 3:
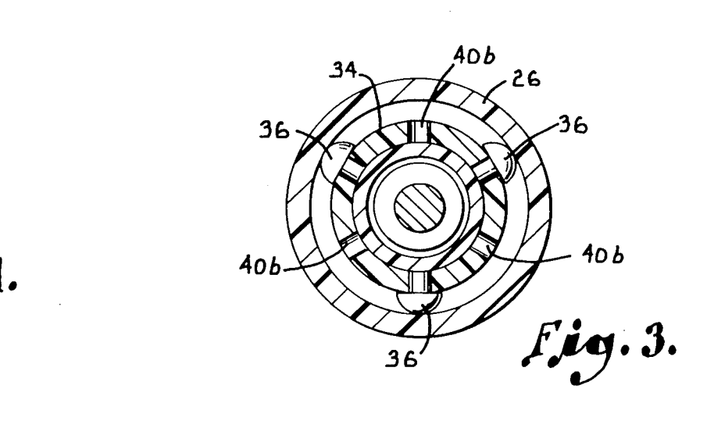
FIG. 3 is a sectional view taken generally along line 3—3 of FIG. 2 in the direction of the arrows.

Referring now to FIGS. 2 and 3, the acoustical transducer includes a cylindrical body 26 which may be constructed of a suitable plastic material. Glued or otherwise secured to the opposite ends of the body 26 are end caps 27 and 28. Fittings 29 and 30 are pressed into the end caps 27 and 28 and may be mated with standard ventilator ports in order to connect the transducer in a ventilator line. O rings 32 provide seals between the fittings and the end caps 28.

Mounted concentrically within the cylindrical body 26 is a smaller tube or cylinder 34 which is spaced inwardly from the inside wall of body 26 by two sets of spacers 36. Each set of spacers 36 includes three spacers which are spaced apart 120° circumferentially and which locate the inner cylinder 34 in a coaxial relationship with the body 26. The spacers 36 in the two sets of spacers are located near the opposite ends of the inner cylinder 34. The opposite ends of cylinder 34 are closed by dome shaped end caps 38 which maintain the turbulence of the gas that is being analyzed within acceptable limits. The wall of cylinder 34 is provided with a plurality of inlet ports 40a which permit the gas to flow into the cylinder 34 and a plurality of outlet ports 40b which permit the gas to flow back out of the cylinder. The ports 40a and 40b are located near the opposite ends of cylinder 34 and spaced apart circumferentially around the cylinder.

An acoustic transmitter 42 is mounted within cylinder 34 at one end and includes a transmitting crystal 44. An acoustic receiver 46 is mounted in the opposite end of cylinder 34 and is equipped with a receiving crystal 48. The crystals 44 and 48 are preferably a matched pair of piezoelectric crystals which are mechanically resonant at 25 kHz. It should be noted that transmitting and receiving elements having other resonant frequencies can be used if desired.

The spacing between the transmitter 44 and receiver 48 is 1.50 inches. This distance has been selected because with air at 25° C. and with sound waves having a frequency of 25 kHz, 1.50 inches is approximately 2.75 times the wavelength or 90°·shy of three wavelengths. The total wavelength shift from 0 to 100% oxygen (with a mixture of nitrogen and oxygen) is 0.157 wavelength, or a total phase shift of 20°. Using a pulse amplitude of 2.5 volts (as will be explained more fully), a full scale signal span of 278 mv results, and this has proven to be an adequate signal.

The inside surface of cylinder 34 is lined with an acoustic open cell foam 50 in order to minimize the reflection of sound waves from the inner cylinder wall. Mounted on the inside surface of the lining 50 is a temperature sensor 52 which may be a commercially available electronic component sold by National Semiconductor under the designation LM34. The temperature sensor 52 is preferably laser trimmed so that it provides a consistent output signal having a linear slope of +10 millivolts/° F. Electrical power is supplied to the transmitter 44, the receiver 48 and the temperature sensor 52 by small wires 54 which extend through the wall of the outer body 26, through the annular space that is presented between body 26 and cylinder 34, and through the wall of cylinder 34 and the acoustical lining 50. Suitable sealing compound 56 is used to seal the opening through which the wires extend into the outer body 26. This interior of cylinder 34 presents a sample chamber 57 within the lining 50.

Figure 4:
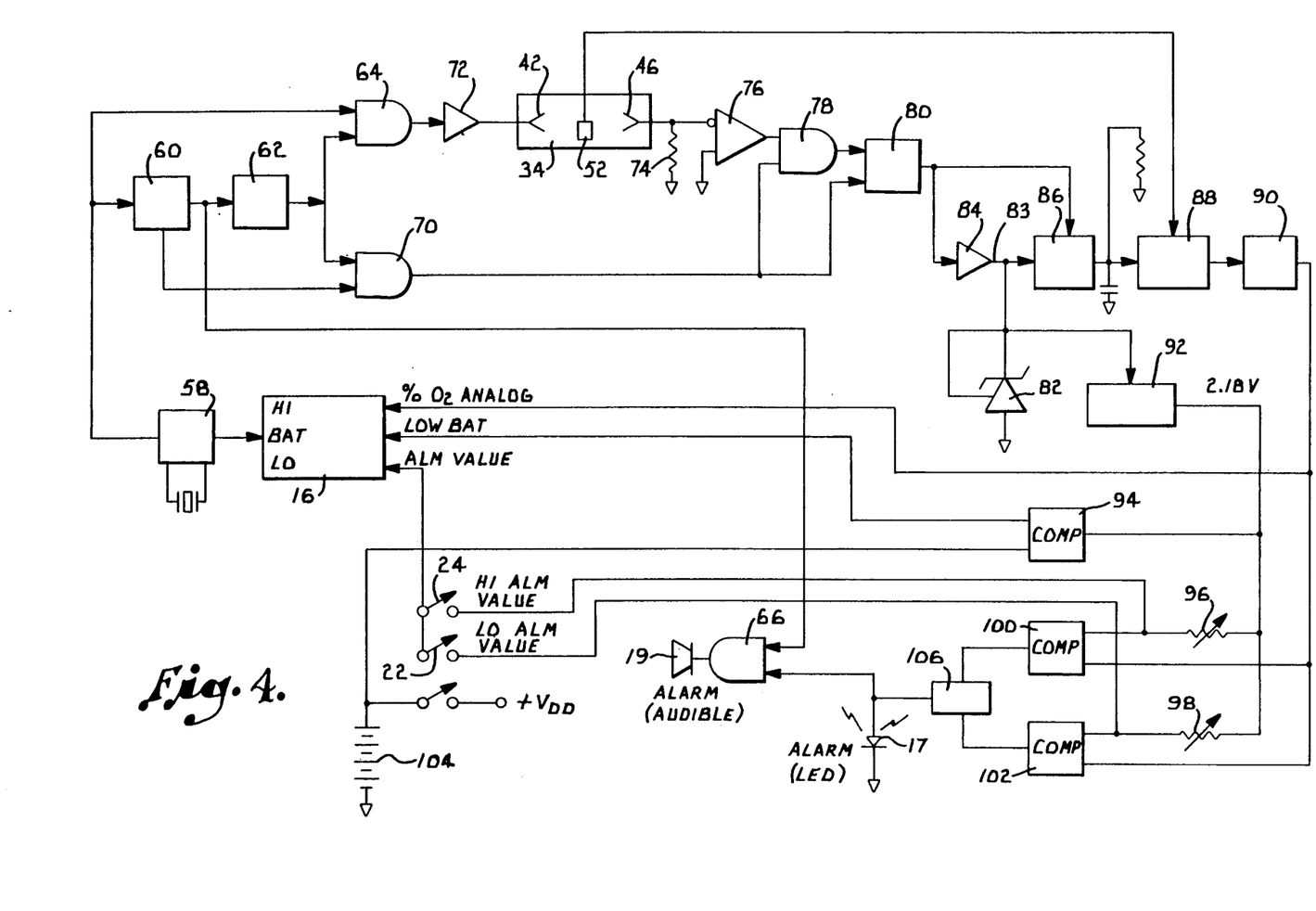
FIG. 4 is a block diagram of the electronic circuitry in the gas monitoring device.

The electronics of the gas monitoring device are shown in block diagram form in FIG. 4. A 25 kHz crystal controlled clock 58 provides a clock signal to the LCD 16 and for the rest of the system as well. The 25 kHz clock signal is applied to serially arranged counting circuits 60 and 62 and also as one input to an AND gate 64. The output signal from the first counting circuit 60 is applied as a 2.5 kHz signal to one input of an AND gate 66 which controls an audible alarm 68. The first counting circuit also supplies one input to another AND gate 70. The second input to each of the gates 64 and 70 is supplied by the second counting circuit 62. The output from gate 64 is conditioned by buffer circuitry 72 and is provided to the transmitter 42 as a ten cycle burst of 25 kHz square waves every four milliseconds. Transmitter 42 is damped by the very low impedance of buffer 72. This signal energizes the acoustical transmitter 42 which then applies corresponding bursts of acoustic waves that are picked up by the receiver 46.

The electrical output signal from the receiver 46 is partially damped by a resistor 74 and is amplified and inverted in a zero crossing inverting comparator 76. The output signal from circuit 76 forms one input to an AND gate 78, the other input of which is supplied by gate 70 representing the tenth pulse that is transmitted by the transmitter 42. Consequently, the output signal from gate 78 is a signal that represents an isolation of the seventh pulse which is received by the receiver 46. The output signal from gate 78 is applied to a phase discriminator 80 (which may be a flip flop circuit). The output signal from gate 70 is also applied to the phase discriminator 80 which measures the phase difference between the signals from gates 70 and 78 to provide a measure of the transit time of the acoustical waves and thus a measure of the percentage of oxygen in the oxygen/nitrogen gas mixture between the transmitter 42 and receiver 46.

The gas monitoring device is a battery operated instrument, and it is necessary to standardize the amplitude of the output signal from the phase discriminator 80. This is accomplished by a precision shunt regulator 82 which clips the output signal from the phase discriminator 80 to a 2.5 volt signal 83 at the output of a buffer 84 that receives the output signal from the phase discriminator 80. Therefore, 2.5 volt signal 83 occurs only once every 100th cycle from the clock circuit 58. The 2.5 volt signal 83 is applied to a sample and hold circuit 86 along with the output signal from the phase discriminator 80. The sample and hold circuit 86 has a controlled leakage and thereby acts as a pulse averaging (pulsewidth-to-voltage) discriminator. The sample-and-hold circuit thus provides an output analog DC signal that is proportional to the transit time of the acoustic signal, and the transit time is in turn proportional to the mean molecular weight of the gas mixture. The output signal from circuit 86 is thus indicative of the relative proportions of the two known gases in the mixture.

The sample and hold circuit 86 also acts as an amplifier which brings the repeatable and mathematically predictable temperature coefficient of $-3.628$ mv/° F. up to $-10$ mv/° F. which matches the $+10$ mv/° F. characteristic of the temperature sensor 52. The output signals from the temperature sensor 52 and the sample and hold circuit 86 are added together in an adder circuit 88, thus totally canceling the effects of temperature changes. An amplifier 90 removes the DC offset signal and provides both scale and span adjustments. The output signal from the amplifier 90 is thus a temperature compensated analog of the oxygen concentration in the oxygen/nitrogen gas mixture having a span of from 0 volts (pure nitrogen) to 1 volt (pure oxygen.) The scale is linear. The 0–1 volt output from the amplifier 90 is applied to the LCD 16 and provides a three digit readout of the percent of oxygen in the mixture.

A peak detector 92 adjusts the 2.5 signal 83 to a constant and stable reference voltage of 2.18 volts which is applied to a low battery comparator 94 and, through potentiometers 96 and 98, to respective comparators 100 and 102. The output signal from amplifier 90 supplies the other input to each comparator 100 and 102. The second input to comparator 94 is supplied by a battery 104, and comparator 94 supplies the LCD 16 with a signal in the event that the battery charge drops below a preselected level. The LCD 16 then displays a "low bat" indication on the face of the instrument.

The potentiometer 96 is used to set the high limit for the oxygen concentration, and its setting is made available to the LCD 16 through switch 24. When switch 24 is depressed, the high oxygen limit is displayed by the LCD 16. Similarly, switch 22 makes available to the LCD the low oxygen limit which is set by the other potentiometer 98. When switch 22 is depressed, the low oxygen setting is displayed by the LCD 16.

An out of limit alarm 106 is activated whenever the output signal from amplifier 90 is above the high oxygen limit set by potentiometer 96 or below the low oxygen alarm limit set by potentiometer 98. Then, the alarm LED 17 is energized, and the audible alarm 19 is energized at the frequency of the output from the first counting circuit 60 (2.5 kHz).

Figure 5:
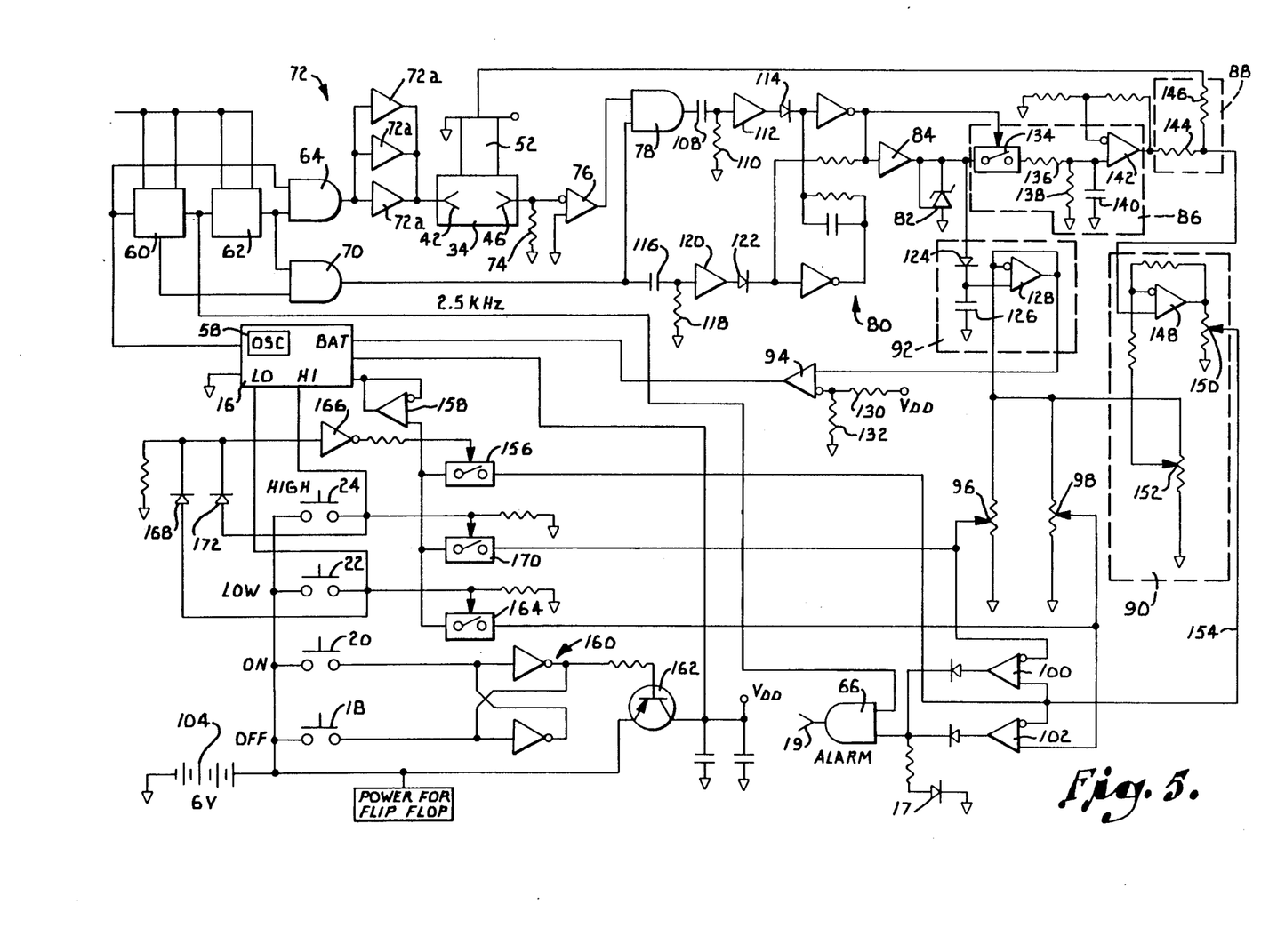
FIG. 5 is a schematic diagram of the circuitry.

FIG. 5 is a schematic diagram of the circuitry which is shown in block diagram form in FIG. 4. The 25 kHz crystal controlled square wave oscillator 58 serves as the master clock and may be either self contained or, as shown, located within the LCD display circuitry. The clock signal is applied to the first counter 60 and also to gate 64. The output signal from the second counter 62 is applied as the other input to gate 64 and also as one input to gate 70, the other input of which comes from the first counter 60. The output signal from the first counter 60 is a 2.5 kHz square wave which is applied to gate 66 and used to control the frequency of the audio alarm 19. The output signal from the second counter 62 is high during ten cycles (400 microseconds) of the clock 58, and it operates on a duty cycle of 1:10 (every 4 milliseconds). The output signal from gate 64 drives three parallel connected noninverting buffers 72a which collectively form the buffer 72 that excites the transmitter 42. The combined output impedance of the buffers 72a closely matches that of the transmitter 42 and thus damps the transmitter when each pulse burst ceases. The output signal from gate 70 is a pulse that is commensurate with the tenth cycle in each burst of ten transmitted pulses.

The spacing between the transmitter 44 and receiver 48 (2.75 wavelengths) imposes a delay of 110 microseconds, so that the seventh pulse in each pulse burst is received by the inverting comparator 76 20 microseconds after the beginning of the tenth transmitted pulse. Thus, signals commensurate with the tenth transmitted pulse and the seventh received pulse are applied to gate 78, the output of which is differentiated by a circuit formed by capacitor 108 and resistor 110 and applied to a noninverting buffer 112. The output from buffer 112 is applied through a diode 114 to the flip flop which forms the phase discriminator 80.

The output signal from gate 70 is differentiated by a circuit formed by capacitor 116 and resistor 118 and is then applied to a noninverting buffer 120 and through diode 122 to the phase discriminator 80. The phase comparison between the tenth transmitted pulse and the seventh received pulse is made on a 100:1 duty cycle, thus minimizing current drain and assuring that there is sufficient quiescent time between successive bursts of pulses to allow full dissipation of reverberations and other transients.

The output from the flip flop circuit 80 is a rectangular pulse generated every four milliseconds, and the width of each pulse varies with the transit time of the selected ultrasound pulse.

The precision shunt regulator 82 clips the output pulse from buffer 84 to a constant amplitude of 2.5 volts over a battery range down to 4 volts, thus eliminating error as the 6 volt battery decays with age. The peak detector 92 is formed by a diode 124, a capacitor 126 and an operational amplifier (op amp) 128, and the output signal from the op amp 128 is at a constant level of 2.18 volts which is applied to the low battery comparator 94. The voltage of the battery 104 is applied through a voltage divider formed by resistors 130 and 132 as the other input to comparator 94, and a low battery signal is applied by comparator 94 to the display circuitry 16 whenever the battery voltage drops below a level of 4.3 volts. The voltage drop from 2.5 volts to 2.18 volts results from the forward junction drop of the diode 124.

The sample-and-hold circuit 86 is formed by an analog switch 134, resistors 136 and 138, a capacitor 140, and an op-amp 142. The op amp 142 applies its output signal to the adder circuit 88 formed by resistors 144 and 146. The other input to the adder circuit is applied by the temperature sensor 52. As previously indicated, sensor 52 generates a voltage of $+10$ mv/° F. The demodulated signal contains a temperature error of $-3.628$ mv/° F. The op amp 142 amplifies the temperature error to a level of $-10$ mv/° F. in order to cancel the $+10$ mv/° F. signal from the sensor 52 in the adder circuit 88 so that the effects of temperature are compensated for completely.

The output signal from the adder circuit 88 is applied to the amplifier circuit 90 which includes a comparator 148 and a pair of potentiometers 150 and 152. The 2.18 volt reference signal from op amp 128 is also applied to the potentiometer 152, as well as to the high and low alarm setting potentiometers 96 and 98 respectively.

The output signal from the amplifier circuit 90 is applied on line 154 as an analog voltage that represents the percentage of oxygen in the oxygen/nitrogen gas mixture that is being analyzed. Line 154 also connects with comparators 100 and 102 and through an analog switch 156 with an op amp 158. The output from comparator 158 is applied to the display circuitry 16 which then generates a digital readout displaying the percentage of oxygen in the mixture.

The off and on membrane switches 18 and 20, respectively, control a flip flop 160 which in turn controls the state of a transistor 162. When the on switch 20 is depressed, transistor 162 is conductive and applies battery power to the entire circuit. When the off switch 18 is depressed, transistor 162 becomes nonconductive, and power to the circuit is removed. When the low membrane switch 22 is depressed, a corresponding analog switch 164 closes, and the signal circuit from the low oxygen potentiometer 98 is then applied through switch 164 to the op amp 158. At the same time, the output from an inverter 166 is driven low through diode switch 22 and 168 to open switch 156. When membrane switch 24 is depressed, a corresponding analog switch 170 closes, and the output signal from potentiometer 96 is then applied to op amp 158. The output from inverter 166 is also driven low through switch 24 and diode 172 to assure that switch 156 is open. Inverter 166 thus maintains switch 156 in a normally closed position so that the oxygen concentration percentage is normally displayed on the LCD 16. However, if either the low or high membrane switch 22 or 24 is depressed, switch 156 is open and the corresponding switch 164 or 170 is closed to cause the display 16 to provide a digital readout of the low or high oxygen alarm setting which has been selected by adjusting the corresponding potentiometer 98 or 96.

Figure 6:
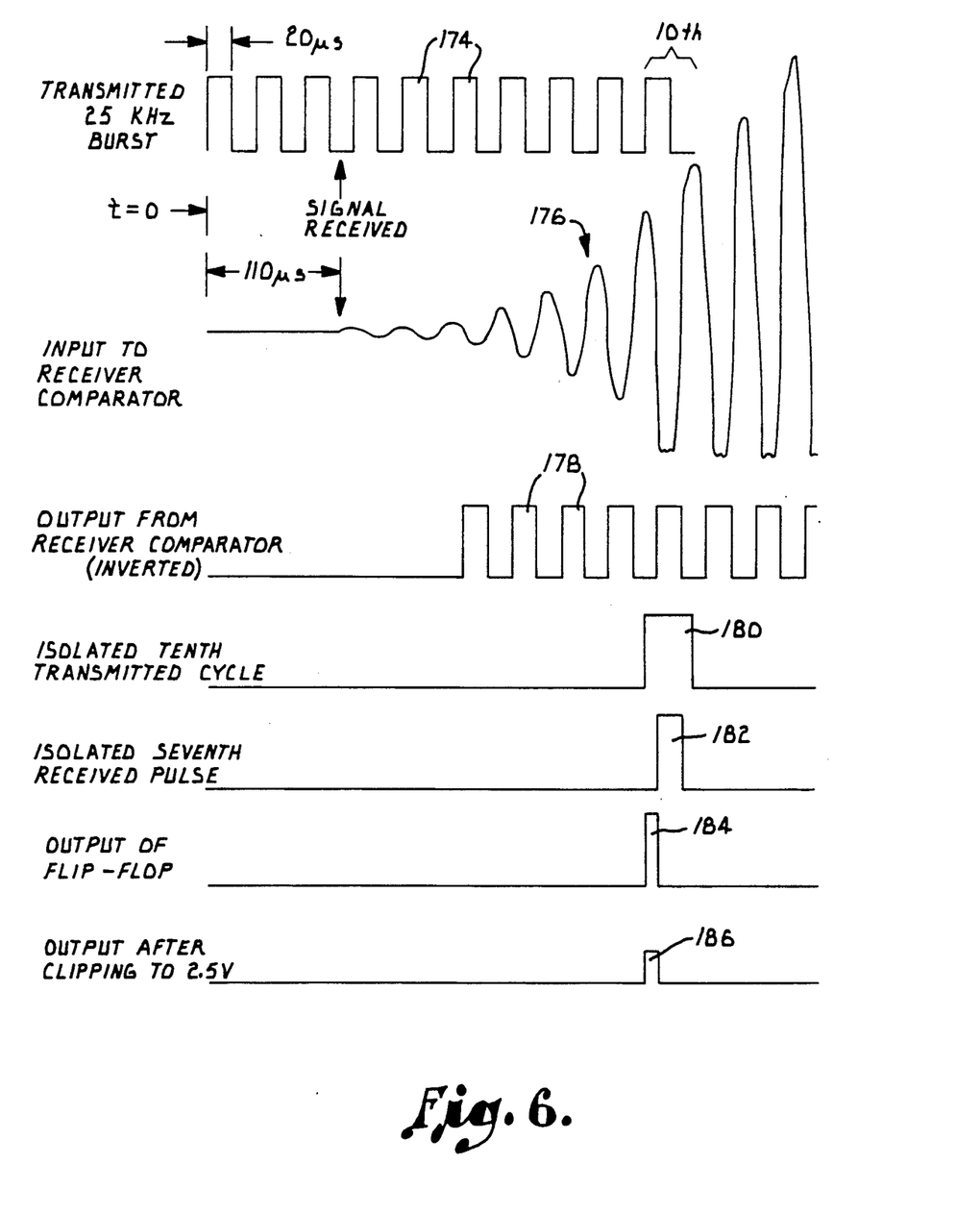
FIG. 6 is a diagramatic view of the waveforms at various parts of the circuitry.

In operation of the gas monitoring device 10, air or another binary gas mixture applied through fitting 29 and passes through the annular space between body 26 and cylinder 24 and also through the interior of cylinder 34, then out through the outlet fitting 30. The transmitter 44 is excited at its resonant frequency of 25 kHz and emits successive bursts of acoustic waves, each containing ten consecutive pulses as indicated by the pulses identified by numeral 174 in FIG. 6. The quiescent time between the successive bursts of pulses is long enough to assure that all reverberations and transients have dissipated before the initiation of each following burst of pulses, and this avoids standing waves that can interfere with proper operation of the device. The acoustic waves are received by the receiver 48, following the transit time from the transmitter to the receiver, and the receiver 48 applies to comparator 76 an electrical signal which represents the acoustic energy it receives. After partial damping by resistor 74, the waveform which is input to comparator 76 is shown in FIG. 6 and identified by numeral 176. The signal 176 is amplified in the zero crossing inverting comparator 76 such that the output from comparator 76 is a square wave signal identified by the pulses 178 in FIG. 6. The output signal from gate 70 represents the tenth transmitted pulse, as indicated by the pulse identified by numeral 180 in FIG. 6. Pulse 180 is combined in gate 78 with the output from comparator 76 to isolate the seventh received pulse, as indicated by pulse 182 in FIG. 6.

The phase difference between pulses 180 and 182 is measured in the phase discriminator provided by flip flop 80 and produces an output signal represented by pulse 184 in FIG. 6. The pulse 184 is clipped to a 2.5 volt amplitude, as indicated by pulse 186 which is provided by the precision shunt regulator 82.

Pulse 186 occurs only once every 100th cycle of the clock, which requires the use of a sample-and-hold circuit 86, together with a controlled leakage to provide pulsewidth-to-voltage conversion. The output from the sample and hold circuit 86 thus provides an output analog DC signal that is proportional to the transit time of the acoustic signal, and this transit time is in turn proportional to the mean molecular weight of the gas mixture so that it provides an identification of the relative proportion of the two gases contained in the air (which is considered to be a binary mixture of oxygen and nitrogen), or any other binary gas mixture which is being monitored.

As previously indicated, there is a zero-offset signal component that represents the initial phase difference of approximately 90°. This voltage is initially canceled to zero by flushing pure nitrogen through the transducer while adjusting potentiometer 152 until the output signal from op amp 158 is such that the display 16 provides a reading of zero percent. Then, pure oxygen is flushed through the transducer and potentiometer 150 is adjusted until the display 16 reads 100% (this occurs when line 154 is at 1.00 volt). Finally, room air is flushed through the transducer and, if necessary, potentiometer 152 is trimmed so that the display 16 reads 20.9% (when line 154 is at 0.209 volt).

The high and low alarm points for the oxygen are set by adjusting potentiometers 98 and 96, respectively, and the value that is selected is displayed on the LCD 16 by depressing the corresponding membrane switch 22 or 24. It is again pointed out that when neither switch 22 or 24 is depressed, the LCD 16 displays the percent oxygen in the gas mixture that is being analyzed. If the oxygen content mixture is below the low alarm limit or above the high alarm limit, the audio alarm 19 generates an audio alarm signal and the LED 17 is energized to provide a visual alarm signal on the face of the instrument.

By generating bursts of acoustic waves periodically and providing between the last pulse in each burst and the initial pulse in the succeeding burst a sufficiently long quiescent time, standing waves are unable to set up in the gas sample chamber 57, and the inaccuracies and lack of reliable repeatability that result from standing waves are avoided. Consequently, enhanced accuracy and repeatability are provided by the present invention. At the same time, resonant transmitting and receiving elements can be used and full advantage is taken of their attributes.

The physical construction of the transducer also adds to the accuracy and reliability of the instrument. The coaxial arrangement of body 26 and cylinder 34 is advantageous in several respects. First, it assures that the gas flow through the sample chamber 57 is gentle and thus avoids the possible error that can be caused by high velocity gas flow. Secondly, it eliminates the possibility of a pressure differential between the inside and outside of the sample chamber that could alter the spacing and orientation of the components enough to cause a slight error. Finally, the temperature of the sample gas can be measured more accurately because the sensor 52 is in direct contact with the sample gas and effective thermal barriers are provided by body 26, cylinder 34, lining 50 and especially by the sample gas itself which flows in gently from the annular space between body 26 and cylinder 34.

All of these advantageous aspects of the invention are important, and they act together to overcome the problems of standing waves and temperature effects that have plagued earlier efforts at using ultrasound techniques to accurately and repeatably monitor the content of a binary gas mixture. As a consequence, the present invention exhibits improved functional capabilities without introducing undue cost or complexity.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, I claim:

1. Apparatus for monitoring the content of a gas sample consisting essentially of two known gases, said apparatus comprising:
   means for providing a sample chamber for receiving the gas sample;
   a resonant transmitter in said sample chamber excitable at a predetermined resonant frequency and operable when excited to transmit sound waves through the gas sample in said sample chamber;
   means for exciting said transmitter with an excitation signal having a plurality of successive bursts each including a preselected number of excitation pulses at said resonant frequency, the initial pulse in each burst being separated from the final pulse in the immediately preceding burst by a quiescent time period of sufficient duration to allow dissipation of any transient effect that may have existed as a result of said immediately preceding burst, thereby suppressing standing waves in the sample chamber;
   a resonant receiver in said sample chamber spaced a preselected distance from said transmitter and operable to receive the sound waves transmitted thereby, said receiver being resonant at said predetermined resonant frequency;
   means for generating from said receiver an electrical signal representative of the transit time between said transmitter and receiver of each sound wave transmitted through the gas sample in said sample chamber; and
   means for using said electrical signal to generate an output signal indicative of the ratio of the two known gases in the gas sample.

2. Apparatus as set forth in claim 1, wherein said means for providing a sample chamber comprises:
   an imperforate body having a substantially cylindrical shape and opposite ends presenting an inlet and an outlet for the sample gas;
   a cylinder mounted within said body in a coaxial relationship therewith with an annular space presented between the body and cylinder, said cylinder presenting said sample chamber therein and having opposite end portions at which the transmitter and receiver are located;
   a plurality of inlet ports in said cylinder adjacent the end portion thereof at which said transmitter is located, said inlet ports providing communication between said annular space and the sample chamber presented in the cylinder; and
   a plurality of outlet ports in said cylinder adjacent the end portion thereof at which said receiver is located, said outlet ports providing communication between said sample chamber and said annular space.

3. The apparatus as set forth in claim 2, including:
   a temperature sensor mounted inside of said cylinder and operable to sense the temperature of the sample gas in the sample chamber and to generate a temperature dependent signal that represents the sensed gas temperature; and
   means for combining said temperature dependent signal with said electrical signal in a manner to effect a correction of said output signal for the effects of the gas sample temperature.

4. The apparatus as set forth in claim 2, including:
   an acoustical lining on the inside of said cylinder effective to suppress reflection of sound waves from the lining;
   a temperature sensor mounted on said lining and operable to sense the temperature of the sample gas in the sample chamber and to generate a temperature dependent signal that represents the sensed gas temperature; and
   means for combining said temperature dependent signal with said electrical signal in a manner to effect a correction of said output signal for the effects of the gas sample temperature.

5. The apparatus as set forth in claim 4, including electrical wiring extending to said temperature sensor through said body, said annular space, said cylinder and said lining.

6. The apparatus as set forth in claim 2, including an end cap on each of the opposite end portions of said cylinder, each end cap having a dome configuration.

7. The apparatus as set forth in claim 1, including:
   means for selecting low and high limits for the concentration of one of the gases in the gas sample; and
   means for generating an alarm signal when the concentration of said one gas is below the selected low limit or above the selected high limit.

8. The apparatus as set forth in claim 1, including means for using said output signal to visually display the concentration of one of the gases in the gas sample.

9. Apparatus for monitoring the content of a gas sample consisting essentially of two known gases, said apparatus comprising:
   a cylinder having a wall and closed first and second ends, said cylinder presenting a sample chamber for the gas sample between said ends;
   a transmitter mounted in said sample chamber adjacent one end of the cylinder and operable when excited to transmit sound waves through the sample chamber;
   a receiver mounted in said sample chamber adjacent the end thereof opposite said one end and operable to receive the sound waves;
   means for generating an electrical signal representative of the transit time between said transmitter and receiver of each sound wave transmitted through the gas sample in said sample chamber, thereby providing a signal indicative of the concentration ratio between the two known gases in the gas sample;

a substantially cylindrical body having opposite inlet and outlet ends for receiving and discharging the gas sample respectively, said body having a diameter greater than said cylinder;

means for mounting said cylinder within said body in a coaxial relationship therewith with an annular space presented between the cylinder and body;

inlet port means in the wall of said cylinder adjacent said first end thereof for allowing ingress of the sample gas from said annular space into the sample chamber; and outlet port means in the wall of said cylinder adjacent said second end thereof for allowing egress of the sample gas from said sample chamber into said annular space.

10. Apparatus as set forth in claim 9, wherein said mounting means comprises a plurality of spacers interposed between said cylinder and said cylindrical body.

11. Apparatus as set forth in claim 9, wherein said inlet port means comprises a plurality of ports in said wall spaced circumferentially apart thereon and located substantially equidistantly from one another.

12. Apparatus as set forth in claim 9, wherein said outlet port means comprises a plurality of ports in said wall spaced circumferentially apart thereon and located substantially equidistantly from one another.

13. Apparatus as set forth in claim 9, wherein said outlet port means comprises a plurality of ports in said wall spaced circumferentially apart thereon and located substantially equidistantly from one another.

14. Apparatus as set forth in claim 9, including:
an acoustical lining on the inside of said cylinder effective to suppress reflection of sound waves from the lining;

a temperature sensor mounted on said lining and operable to sense the temperature of the sample gas in the sample chamber and to generate a temperature dependent signal that represents the sensed gas temperature; and means for combining said temperature dependent signal with said electrical signal in a manner to correct said electrical signal for the effects of the sample gas temperature.

15. A method of monitoring the content of a gas sample consisting essentially of two known-gases, said method comprising the steps of:

transmitting sound waves through the gas sample in a plurality of successive bursts each including a preselected number of pulses at a preselected frequency with the initial pulse in each burst being separated from the final pulse in the immediately preceding burst by a quiescent time period of sufficient duration to allow dissipation of any transient effects that may have resulted from transmission of said immediately preceding burst, whereby standing waves in the sample gas are avoided;

receiving each sound wave transmitted through the sample gas at a location spaced a preselected distance from the location at which the sound wave is transmitted;

measuring the transit time of each sound wave from the time of its transmission to the time of its reception to provide a measure of the relative proportions of the two known gases in the gas sample; and providing a display indicative of the relative proportions of the two known gases in the gas sample.

16. The method of claim 15, steps of sensing the temperature of the sample gas to provide a temperature measurement and combining said temperature measurement with the measurement of the transit time to compensate for the effects of the sample gas temperature.

* * * * *